United States Patent
Pawlak et al.

(10) Patent No.: US 12,251,581 B2
(45) Date of Patent: Mar. 18, 2025

(54) FLASH ELECTRON APPLICATOR WITH INTEGRATED DOSIMETER

(71) Applicant: Varian Medical Systems, Inc., Palo Alto, CA (US)

(72) Inventors: Daniel Charles Pawlak, Dixon, CA (US); Lasitha Senadheera, Mountain View, CA (US); Reza Alibazi Behbahani, North Brunswick, NJ (US); William T. Main, Mariposa, CA (US); Nicholas James Pouliot, Dublin, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 252 days.

(21) Appl. No.: 17/710,651

(22) Filed: Mar. 31, 2022

(65) Prior Publication Data

US 2023/0317310 A1 Oct. 5, 2023

(51) Int. Cl.
*A61N 5/10* (2006.01)
*A61B 6/42* (2024.01)
*G21K 1/02* (2006.01)
*G21K 1/04* (2006.01)

(52) U.S. Cl.
CPC .............. *A61N 5/1077* (2013.01); *A61B 6/42* (2013.01); *A61N 5/1071* (2013.01); *G21K 1/025* (2013.01); *A61N 2005/1089* (2013.01); *G21K 1/046* (2013.01)

(58) Field of Classification Search
CPC ...... A61N 5/10; A61N 5/1048; A61N 5/1049; A61N 5/1064; A61N 5/1065; A61N 5/1067; A61N 5/1071; A61N 5/1077; A61N 5/1078; A61N 5/1081; A61N 5/1082; A61N 5/1083; A61N 2005/1089; A61N 2005/1092; A61N 2005/1094; A61N 2005/1095
USPC ....................................... 250/492.3
See application file for complete search history.

(56) References Cited

U.S. PATENT DOCUMENTS

| | | | | |
|---|---|---|---|---|
| 4,140,129 A | * | 2/1979 | Heinz | G21K 1/02 |
| | | | | 976/DIG. 428 |
| 4,220,866 A | * | 9/1980 | Taumann | A61N 5/10 |
| | | | | 378/150 |
| 4,314,158 A | * | 2/1982 | Lucido | A61N 5/10 |
| | | | | 850/61 |
| 4,484,078 A | * | 11/1984 | Tayag | A61B 6/102 |
| | | | | 378/147 |

(Continued)

FOREIGN PATENT DOCUMENTS

WO 2014/195986 A1 12/2014

OTHER PUBLICATIONS

Bagala, P. et al., "Radiotherapy electron beams collimated by small tubular applications: characterizaion by silicon and diamond iodes," Physics in Medicine and Biology, Institute of Physics Publishing, vol. 58, No. 7, pp. 8121-8133, Nov. 7, 2013.

*Primary Examiner* — Allen C. Ho
(74) *Attorney, Agent, or Firm* — Harness, Dickey & Pierce, P.L.C.

(57) ABSTRACT

An electron applicator, which is used along with a linear accelerator in a FLASH radiotherapy treatment program, includes an integrated dosimeter for accurately measuring the FLASH radiation levels, and an interchangeable high-density polymer cutout which can be easily, inexpensively, and accurately formed to match the irregular shape of a tumor.

28 Claims, 3 Drawing Sheets

(56) References Cited

U.S. PATENT DOCUMENTS

| | | | | |
|---|---|---|---|---|
| 4,638,814 A * | 1/1987 | Spanswick | A61N 5/1049 | 607/154 |
| 6,977,987 B2 * | 12/2005 | Yamashita | A61N 5/10 | 378/65 |
| 7,831,016 B2 * | 11/2010 | Saoudi | A61N 5/1048 | 378/65 |
| 7,898,192 B2 * | 3/2011 | Maltz | A61N 5/1081 | 378/65 |
| 8,269,197 B2 * | 9/2012 | Goer | A61N 5/10 | 250/492.1 |
| 8,588,368 B2 * | 11/2013 | Fantini | A61N 5/1048 | 378/65 |
| 8,791,437 B2 * | 7/2014 | Felici | A61N 5/10 | 378/65 |
| 10,485,993 B2 * | 11/2019 | Goer | A61N 5/1049 | |
| 11,135,449 B2 * | 10/2021 | Johnson | A61N 5/1083 | |
| 11,524,181 B2 * | 12/2022 | Ciresianu | A61N 5/1083 | |
| 12,036,421 B2 * | 7/2024 | Bruza | A61N 5/1049 | |
| 2010/0278305 A1 | 11/2010 | Fantini et al. | | |
| 2011/0017920 A1 | 1/2011 | Goer et al. | | |
| 2019/0054318 A1 | 2/2019 | Goer et al. | | |
| 2019/0314645 A1 | 10/2019 | Ciresianu et al. | | |

\* cited by examiner

FLASH ELECTRON APPLICATOR WITH INTEGRATED DOSIMETER

BACKGROUND OF THE INVENTION

1. Field of the Invention

The present invention relates to an electron applicator and, more particularly, to a FLASH electron applicator with an integrated dosimeter.

2. Description of the Related Art

A tumor is an abnormal growth of tissue that typically has an irregular shape. Tumors at or near the surface of the skin are often treated with a therapeutic electron beam. A radiotherapy linear accelerator is a medical device that generates and outputs a parallel or collimated electron beam. To avoid damaging healthy tissue adjacent to a tumor, the electron beam must be shaped to match the irregular shape of the tumor.

An electron applicator, is a device that attaches to the linear accelerator to further collimate and shape the electron beam. The electron applicator commonly has an elongated body with a proximate end that attaches to the accelerator and a distal end that is positioned close to the skin. The elongated body has an opening that extends from the proximate end to a partially-closed distal end where the shape of the opening at the distal end defines the final shape of the beam.

In addition, the irregular shape of a tumor may vary as the viewing angle of the tumor changes. Thus, if an electron beam is to be directed to a tumor from three different angles, three different beam shapes may be used where each beam shape matches the irregular shape of the tumor when viewed from that angle.

A common approach to forming different beam shapes for treating a single tumor from different angles is to fabricate multiple "cutouts". The cutouts are casted to the desired shapes using low-melting-temperature lead alloys such as Cerrobend. The cutouts are then inserted into the distal end of the electron applicator per gantry angle as required to achieve the desired shape. The cutouts are expensive and time consuming to fabricate and require certain safety measures such as casting the Cerrobend under a vented hood.

FLASH is an emerging radiation therapy treatment modality where very high dose rates are used to reduce damage to healthy tissue. Conventional electron applicators are designed to treat at distances corresponding roughly with the treatment machine isocenter. To achieve a uniform ('flat') intensity distribution within the collimated area, the electron applicators are physically long, extending to within about 5 cm of the isocenter. In electron FLASH, to achieve the necessary high dose rates, it is advantageous to treat at shorter distances.

FLASH dose rates also present a challenge for accurate, real-time dosimetry. Conventional linear accelerators have ion chambers that monitor the radiation beam and serve as dosimeters that measure the dose. However, conventional ion chambers may have performance limitations associated with the very high dose per pulse delivered during FLASH radiotherapy. The ion chamber may experience high ion recombination, resulting in a non-linear response with respect to dose per pulse. This can lead to inaccurate dosimetry readings.

Note that the ion chamber may also serve as a patient safety device. It may be tied to the control system such that it can assert an interlock when the radiation beam is not correct, for example the beam current is too high or too low. Thus, in Flash radiotherapy, where the ion chamber may have accuracy limitations, it is advantageous to have a secondary dosimeter to confirm the dose is correct and provide redundant safety interlocks.

SUMMARY OF THE INVENTION

The electron applicator of the present invention accurately measures dose when delivered at FLASH dose rates, and easily, inexpensively, and accurately collimates a beam that substantially matches the shape of a tumor. The electron applicator includes a collimating body that has a proximate end, a distal end, and a first opening that extends from the proximate end to the distal end. The electron applicator also includes a radiation detector that can serve as a dosimeter and/or a monitoring device for patient safety. As a dosimeter, it may be used for dose measurements alone and/or it could be used to servo the dose. The dose servo acts to maintain a constant dose per pulse or dose rate across many beam pulses. The electron applicator may contain any supporting circuitry for dose measurements, beam intensity safety interlocks, or dose servo. The radiation detector is coupled to the proximate end of the electron applicator. The design is such that the detector subcomponent does not have to be removed from the gantry when interchanging the distal aperture (with cutouts) subcomponent. It is expected that a set of aperture subcomponents with varying diameters would be made available to cover the clinical range of radiation field widths and shapes.

A better understanding of the features and advantages of the present invention will be obtained by reference to the following detailed description and accompanying drawings which set forth an illustrative embodiment in which the principals of the invention are utilized.

BRIEF DESCRIPTION OF THE DRAWINGS

The accompanying drawings described herein are used for providing further understanding of the present application and constitute a part of the present application. Exemplary embodiments of the present application and the description thereof are used for explaining the present application and do not constitute limitations on the present application.

DETAILED DESCRIPTION OF THE INVENTION

Figure 1:
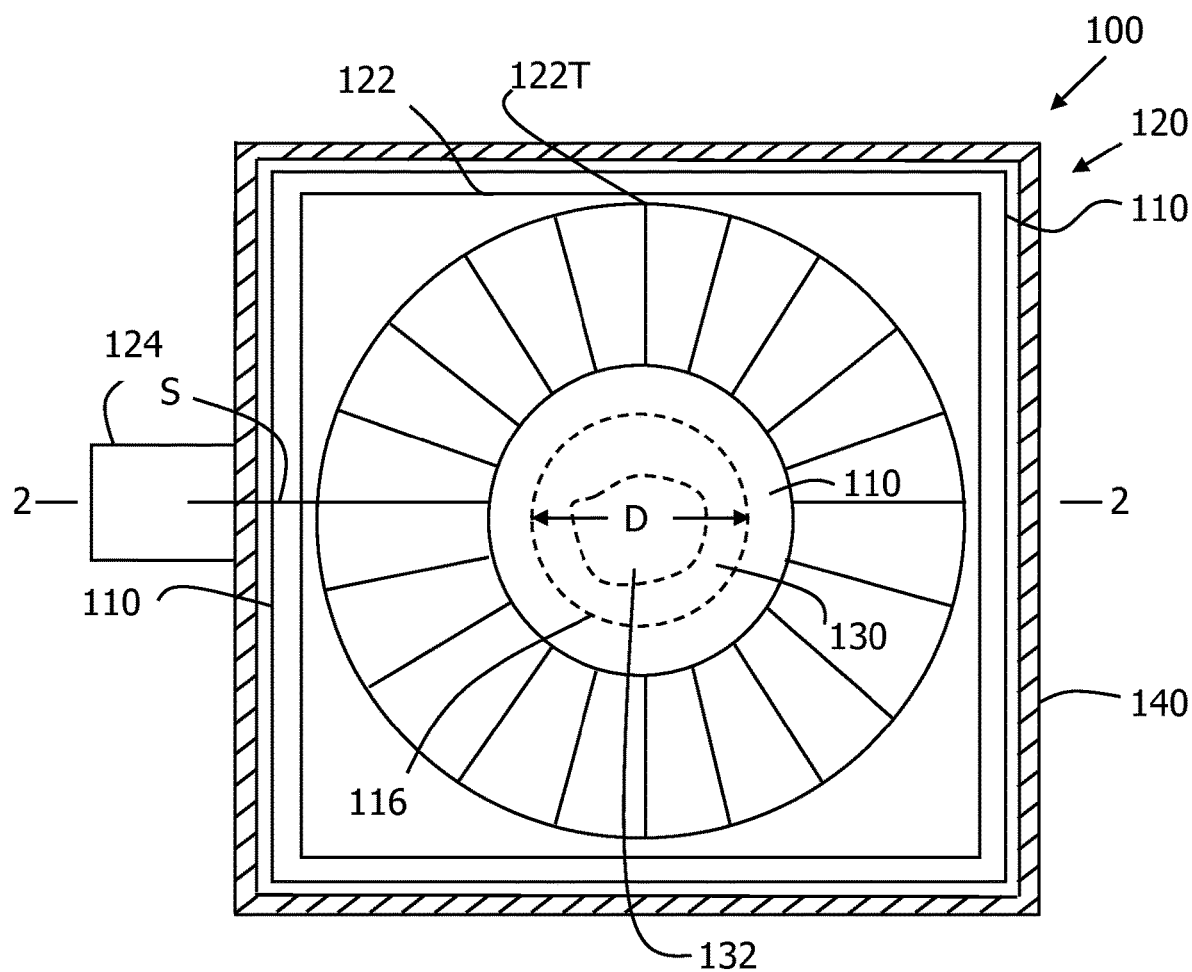
FIG. 1 is a planar view illustrating an example of an electron applicator 100 in accordance with the present invention.

In one embodiment of the present invention, two subcomponents comprise an electron collimator assembly. The first component, 'upstream' of the second component, houses a radiation monitoring device. The second component is a collimation cone, which manually attaches below the monitor component. The design is made such that any of several collimation cones can attach to the monitor component. The range of collimation cones would cover the expected useable radiation field diameters. The collimation cones are circular geometries, similar to x-ray stereotactic cones. Other embodiments can include other non-circular geometries. The cones would be fully enclosed on their sides, allowing for maximum collimation per physical length. In this way, the collimator can be kept short, allowing for the patient to be located closer to the linac gantry head (electron source), thereby taking advantage of higher dose rates available at short source-to-target distances.

The electron collimator design is made such that the entire unit can be manually attached or detached from the linac gantry head. It can be installed when needed for electron FLASH treatments and removed for conventional mode treatments. It is noted that the proposed electron FLASH collimator could be used with conventional electron treatments, possibly offering improved radiation field penumbra and ergonomic advantages of smaller size and lighter weight. The geometric design and material composition allows for minimal radiation leakage outside the intended treatment area, minimal x-ray contamination, and lower weight than conventional electron applicators.

Different types of radiation monitor/dosimetry devices can be implemented. Some examples include: 1) a toroid, 2) a transmission foil, and 3) a capacitive-coupled detector. The toroid, a type of electric transformer, detects the accelerator electron beam passing through its hollow center. The transmission foil, which stretches across the collimator aperture, detects the accelerator electron beam passing through it. The capacitive-coupled detector is a multi-segmented device that senses the proximity of the accelerator beam to the sides of the collimator aperture.

Whereas known electron FLASH applicators in use today are typically not designed to support a beam monitoring device within its assembly, it has been discovered that having an independent, secondary detector is highly advantageous and required. This is because the standard ion chamber present in the linear accelerator may experience high ion recombination, resulting in a non-linear response with respect to dose per pulse. Hence, having the independent, secondary real-time dosimeter to monitor the dose addresses this issue.

In one embodiment, custom 'cut-outs' can be manually installed at the distal end of the cone component, to shape the radiation field to the treatment area. For low energy electron FLASH beams, it is possible and advantageous to make the cut-outs out of the same high density plastic used for the cones. The plastic cut-outs reduces x-ray contamination, and also advantageously allows for 3-D printing, additive manufacture, or easy machining of the cut-out.

Figure 2:
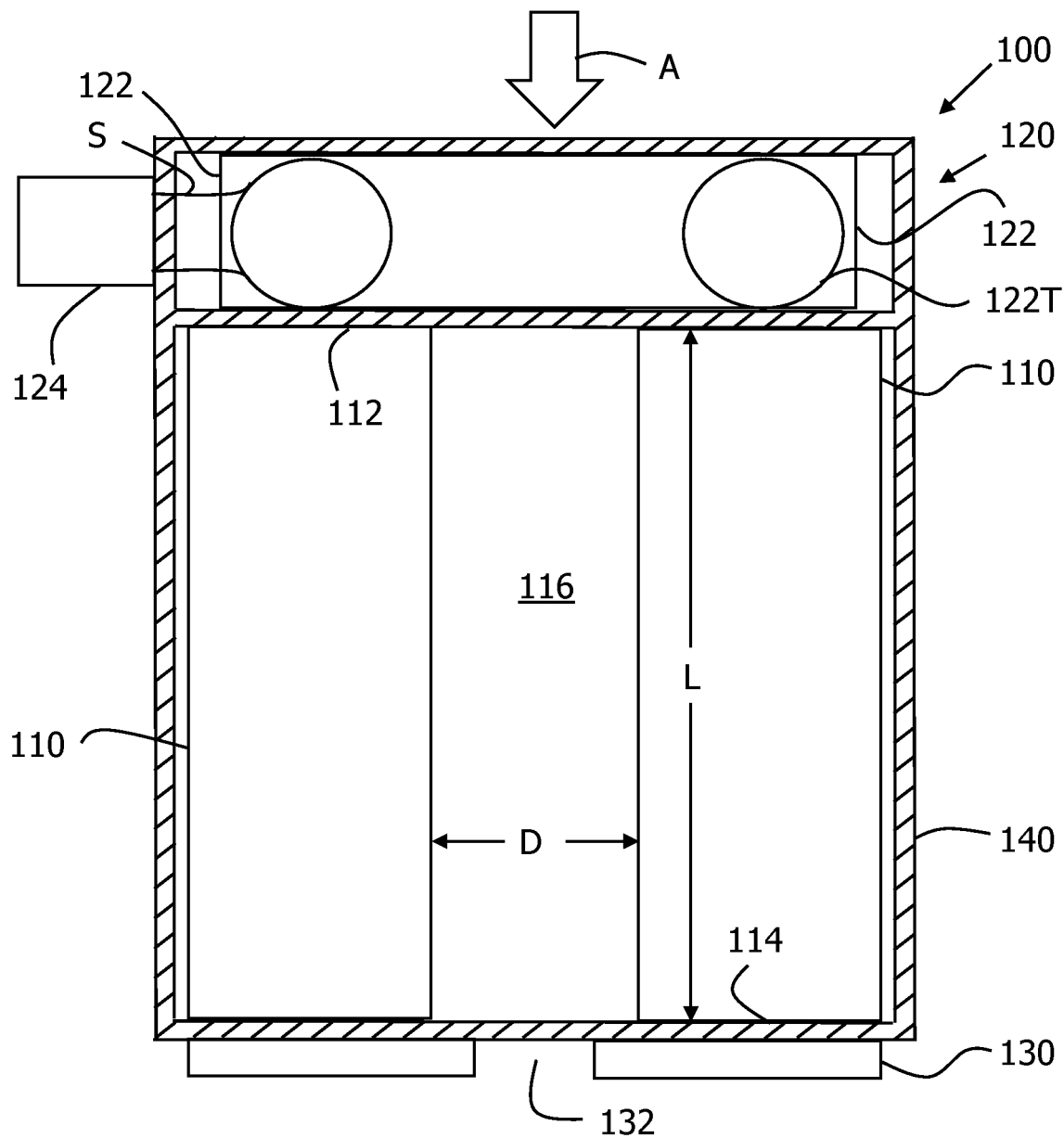
FIG. 2 is a vertical illustration taken along a line perpendicular to—and geometrically centered through—the cross section illustrated in FIG. 1.

FIG. 1 shows a planar view that illustrates an example of an electron applicator 100 in accordance with the present invention. FIG. 2 shows a cross-sectional view taken along line 2-2 of FIG. 1. As described in greater detail below, electron applicator 100 includes an integrated dosimeter for accurately measuring FLASH radiation levels, and an interchangeable high-density polymer cutout which can be easily, inexpensively, and accurately formed to match the irregular shape of a tumor.

As shown in FIGS. 1 and 2, electron applicator 100 includes a collimating body 110 that has a proximate end 112 and a distal end 114. Collimating body 110 also has an opening 116 that extends through collimating body 110 from the proximate end 112 to the distal end 114. Opening 116 is preferably round, but can alternately be other shapes such as square or hexagonal. Opening 116 has a diameter D with a range of sizes, such as 1 cm to 10 cm, and a length L.

The minimum size of diameter D is determined by the size of the tumor as the diameter D must preferably be at least as large as the largest feature of the tumor from a particular view. The maximum size of diameter D is determined by the maximum amount of scattering that can be tolerated as wider openings tend to produce more scattering.

Collimating body 110 is fully enclosed on the sides to allow for maximum collimation per physical length. In this way, collimating body 110 can be kept short, allowing for a patient to be located closer to the gantry head (electron source) of a linear accelerator, thereby taking advantage of higher dose rates. The thickness of the material surrounding opening 116 is determined by the level of radiation leakage that is acceptable.

In the present embodiment, collimating body 110 is fabricated from a high-density polymer, such as polyethylene, but can alternately be fabricated in a conventional manner. Commercial electron applicators are made of metal which provide good radiation shielding, but also generate unwanted x-rays. Scattered electrons in a metal collimator interact with the metal in the collimator and generate unwanted x-rays. Thus, one advantage of a high-density polymer collimator over a conventional metal collimator is that x-ray contamination is substantially reduced.

Another advantage of a high-density polymer collimating body 110 is that it can be easily, inexpensively, and accurately formed by machining a block of the material. Alternately, molds can be used to form collimating body 110. In some embodiments the collimating body may be produced by additive manufacturing or 3D printing.

As further shown in FIGS. 1 and 2, electron applicator 100 also includes a dosimeter 120 that is coupled to the proximate end 112 of collimating body 110. Dosimeter 120 includes a radiation detector 122 that is coupled to collimating body 110, and a processing circuit 124 that is coupled to radiation detector 122 to process signals S from radiation detector 122 and generate a dose reading. In other embodiments, the signal processing circuitry could be remotely located, such as in the gantry. In those embodiments, the electron applicator would provide an interconnect to deliver the signal to the remote processing circuitry.

In the present embodiment, radiation detector 122 is implemented with a toroidal transformer 122T where the central axis of toroidal transformer 122T and opening 116 are aligned. In operation, a radiotherapy linear accelerator outputs a collimated electron beam as shown by arrow A in FIG. 2. The collimated electron beam passes through the center area of radiation detector 122 where the flow of electrons generates an electric signal that is measured by radiation detector 122.

Any of the radiation detector devices that would be incorporated into the electron applicator would respond in a stable, consistent, and calibratable manner to changes in the accelerator beam current. A change in the accelerator beam current (arrow A in FIG. 2) would result in a corresponding change in the dose per pulse or dose rate (for many pulses). The change in beam current would induce a change in the electrical output signal of the detector. This signal would be processed by the associated circuitry and produce a change in the dose reading, a dose servo response (if servo capability was deployed), and/or assert an interlock if the signal threshold was exceeded. The dosimeter 120 can be deployed as a dose servo mechanism. The dosimeter 120 can be deployed as a safety interlock to limit the accelerator beam current to within an acceptable range. Three such embodiments of radiation detector 429122, but not limited to these alone, would deploy either a toroid, a thin transmission foil, or a capacitively-coupled detector. The basic principles of these detectors were explained above. The detectors may be either customized designs or commercially available devices. For example, commercial toroidal-based dosimeters are available.

As additionally shown in FIGS. 1 and 2, electron applicator 100 may further include a cutout 130 that is coupled to the distal end 114 of collimating body 110. Cutout 130 includes an opening 132 that extends through cutout 130, and is shaped to match the irregular shape of a tumor. Cutout 130 can be coupled to collimating body 110 in a conventional manner.

Cutout 130 is interchangeable with other cutouts such that one cutout can be removed and replaced with another cutout. The central axis of radiation detector 122, opening 116, and opening 132 are aligned. In operation, after the electron beam has passed through the center of radiation detector 122, the beam passes through opening 116 in collimating body 110, and then through opening 132 in cutout 130 into a tumor.

In the present embodiment, cutout 130 is fabricated from a high-density polymer, such as polyethylene, but can alternately be formed from other materials. High-density polymer cutout 130 has several advantages over the metal openings in conventional electron applicators including the significant reduction in the amount of x-ray contamination.

Further, cutout 130 and opening 132 can be easily, inexpensively, and accurately formed by obtaining a layer of high-density polymer, which is thinner than the layer used to form collimating body 110, and then machining the layer of high-density polymer to form cutout 130 and opening 132.

One of the advantages of the present invention is that a computer numerical control (CNC) router or similar device can be used to machine opening 132 in a thin layer of high-density polymer to match the irregular shape of a tumor that is much more accurate than the opening that can be formed with an electron applicator that uses a multi-leaf collimator (MLC).

Further, the fabrication of opening 132 in a high-density polymer cutout is substantially easier and cheaper than the process for forming openings in a conventional metal electron applicator. Alternately, cutout 130 can be 3D printed, or formed from molds. The minimum thickness T of cutout 130 is defined by the minimum thickness required to block the electron beam from passing though the regions surrounding opening 132 which, in turn, is defined by the energy of the electron beam.

As further shown in FIGS. 1 and 2, in the present embodiment, electron applicator 100 also includes a housing 140 that holds collimating body 110 and radiation detector 122. Housing 140, which can be implemented in plastic, also facilitates connecting radiation detector 122 to the gantry head of a radiotherapy linear accelerator, and cutout 130 to collimating body 110.

Collimating body 110 is interchangeable with other collimating bodies such that housing 140 can accommodate different collimating bodies. For example, a collimating body 110 that has a diameter D of 10 cm can be removed from housing 140 and replaced with a collimating body 110 that has a diameter D of 4 cm without removing housing 140 from the linear accelerator. Thus, changing opening 116 from a first diameter D to a second diameter D is simple.

Similarly, housing 140 can accommodate different cutouts 130. For example, a cutout 130 that has a first opening that substantially matches the irregular shape of a tumor can be removed from housing 140 and replaced with a cutout 130 that has a second opening that substantially matches the irregular shape of the tumor from a different angle.

Another of the advantages of the present invention is that electron applicator 100, being largely made from plastic, is substantially lighter than conventional electron applicators. In addition, housing 140 is fabricated to easily attach to a linear accelerator. As a result, electron applicator 100 can be installed when needed for electron FLASH treatments, and removed for conventional mode treatments. A further advantage of the present invention is that dosimeter 120 provides a real-time, accurate measure of the dose.

The length L of opening 116 in collimating body 110 is defined by the treatment protocol. For example, conventional radiotherapy utilizes a 100 cm source-to-skin (SSD) measure, while FLASH radiotherapy works better with a shorter 70 cm (or less) SSD. Thus, the applicator-to-skin distance, thickness of cutout 130, length L of collimating body 110, thickness of radiation detector 122, and thickness of housing 140 have a total thickness of approximately 70 cm or less.

Within the limits of the 70 cm protocol, a longer length L increases the flatness of the beam and also increases the intensity of the beam by reducing scatter and generating a more parallel beam. In addition, as the diameter D increases, the length L increases to provide the same beam quality. Further, reducing the distance between cutout 130 and the skin reduces the penumbra and provides a sharper falloff of the radiation field.

Figure 4:
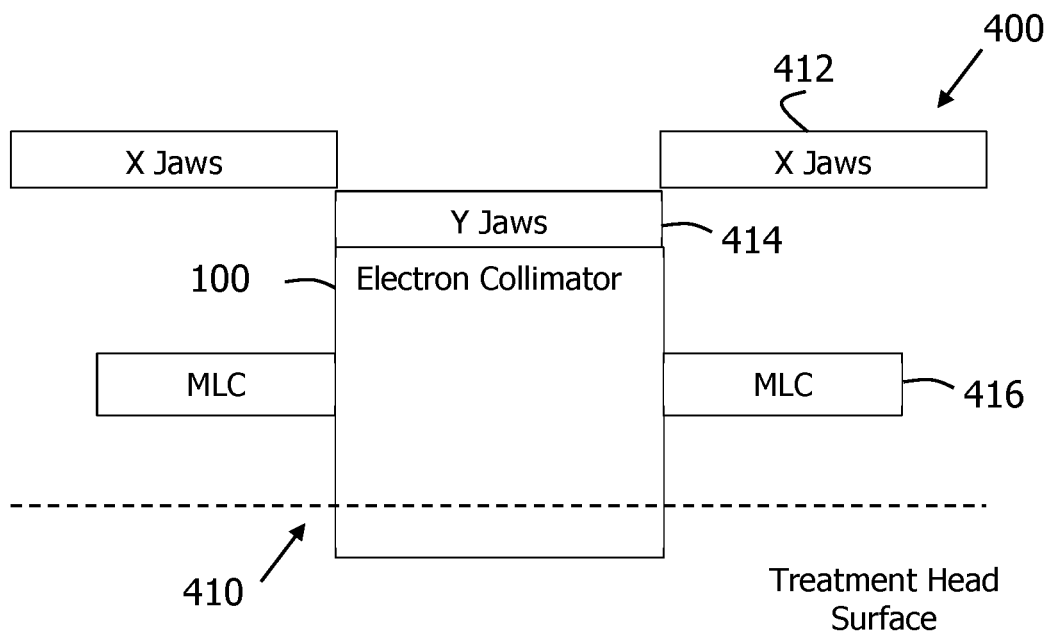
FIG. 4 is an embodiment illustrating that the electron applicator may be designed such that its proximal end is elevated to be within the existing collimator structure of the multileaf collimator. This has the advantage of allowing for shorter treatment distances, and thus higher dose per pulse and dose rates.

An alternative embodiment is shown in FIG. 4 wherein the electron collimator is mounted to the linear accelerator so as to be partially within the treatment head. This is enabled by retracting the linear accelerator's multileaf collimator leaves, and if desired, the primary collimating jaws. This embodiment allows for further reduction of the SSD.

Figure 3:
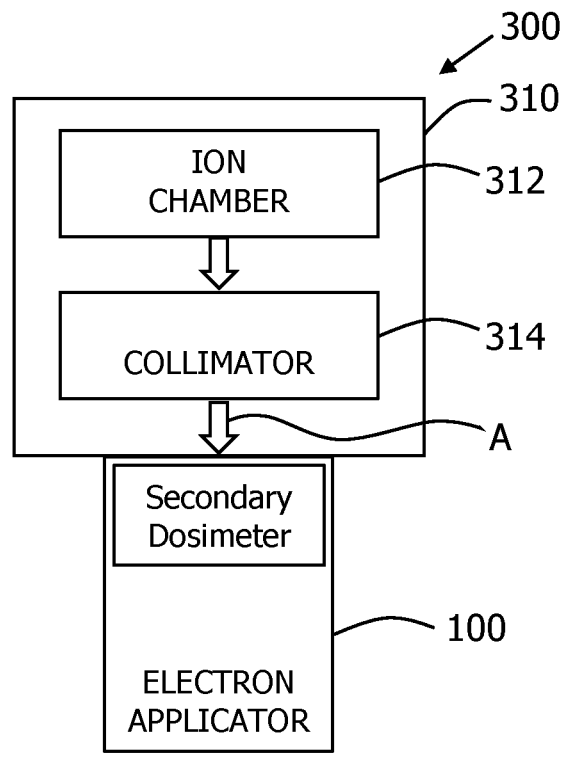
FIG. 3 is a block diagram illustrating an example of a treatment system 300 in accordance with the present invention.

FIG. 3 shows a block diagram that illustrates an example of a treatment system 300 in accordance with the present invention. As shown in FIG. 3, treatment system 300 includes a linear accelerator 310, an internal ion chamber 312, and an internal collimation structure 316. The electron applicator 100 attaches to the output end of the linear accelerator 310 (the output end is typically referred to as the gantry head). The accelerator 310 produces the high energy electron beam. After passing through a filter, the beam passes through the ion chamber 312 where the dose is measured. The beam is shielded and pre-collimated by collimator 316. It then enters the electron applicator 100 per arrow A of FIG. 2. Within the applicator, the beam is monitored with a secondary dosimeter 314 and final shaping of the radiation field per cutout 130

By utilizing the real-time dosimeter incorporated with interchangeable collimator for electron FLASH radiation therapy as described in the various embodiments above, tumors can be treated as follows. First, a high dose of FLASH radiation is generated. This high does FLASH radiation is collimated to form a beam of electrons. This beam of electrons is sent through an electron applicator. Within the electron applicator is a dosimeter that measures the dose in real-time. The electron applicator also shapes the beam to substantially match the shape of the tumor.

Reference has now been made in detail to the various embodiments of the present disclosure, examples of which are illustrated in the accompanying drawings. While described in conjunction with the various embodiments, it will be understood that these various embodiments are not intended to limit the present disclosure. On the contrary, the present disclosure is intended to cover alternatives, modifications and equivalents, which may be included within the scope of the present disclosure as construed according to the claims.

Furthermore, in the preceding detailed description of various embodiments of the present disclosure, numerous specific details are set forth in order to provide a thorough understanding of the present disclosure. However, it will be recognized by one of ordinary skill in the art that the present disclosure may be practiced without these specific details or with equivalents thereof. In other instances, well-known methods, procedures, components, and circuits have not been described in detail so as not to unnecessarily obscure aspects of various embodiments of the present disclosure.

The drawings showing various embodiments in accordance with the present disclosure are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the various embodiments in accordance with the present disclosure can be operated in any orientation.

The above embodiments are merely used for illustrating rather than limiting the technical solutions of the present invention. Although the present application is described in detail with reference to the foregoing embodiments, those of ordinary skill in the art should understand that the technical solutions recorded in the foregoing embodiments may still be modified or equivalent replacement may be made on part or all of the technical features therein. These modifications or replacements will not make the essence of the corresponding technical solutions be departed from the scope of the technical solutions in the embodiments of the present invention.

What is claimed is:

1. An electron applicator comprising:
   a collimating body having a proximate end, a distal end, and a first opening that extends from the proximate end to the distal end;
   a dosimeter having a radiation detector and a processing circuit coupled to the radiation detector to measure radiation levels detected by the radiation detector, the radiation detector being coupled to the proximate end of the collimating body; and
   a cutout having a second opening that extends through the cutout, the cutout being coupled to the distal end of the collimating body.

2. The electron applicator of claim 1, wherein a central axis of the first opening and a central axis of the second opening are aligned.

3. The electron applicator of claim 1, wherein the cutout comprises a high-density polymer.

4. The electron applicator of claim 3, wherein the collimating body comprises a high-density polymer.

5. The electron applicator of claim 3, wherein the radiation detector comprises a toroidal transformer.

6. The electron applicator of claim 5, wherein a central axis of the toroidal transformer and the first opening are aligned.

7. The electron applicator of claim 5, wherein a central axis of the toroidal transformer, the first opening, and the second opening are aligned.

8. The electron applicator of claim 1, further comprising:
   a housing configured to hold the collimating body and the radiation detector.

9. The electron applicator of claim 8, wherein the collimating body is interchangeable with other collimating bodies in the housing.

10. The electron applicator of claim 8, wherein the cutout is interchangeable with other cutouts.

11. The electron applicator of claim 1, wherein the electron applicator is configured to receive FLASH radiation through the radiation detector, and to output FLASH radiation through the cutout.

12. A treatment system comprising:
    a linear accelerator having an ion chamber configured to monitor a dose;
    an electron applicator coupled to the linear accelerator, the electron applicator configured to receive a beam of electrons, and the electron applicator including
       a collimating body having a proximate end, a distal end, and a first opening that extends from the proximate end to the distal end, and
       a dosimeter having a radiation detector and a processing circuit coupled to the radiation detector to measure radiation levels detected by the radiation detector, the radiation detector being coupled to the proximate end of the collimating body; and
    a collimator configured to pre-collimate the beam of electrons before entering the electron applicator.

13. The treatment system of claim 12, wherein the electron applicator further comprises:
    a cutout having a second opening that extends through the cutout, the cutout being coupled to the distal end of the collimating body.

14. The treatment system of claim 13, wherein the cutout is plastic.

15. The treatment system of claim 13, wherein the cutout is manually installed at the distal end of the collimating body.

16. The treatment system of claim 12, wherein the collimating body comprises a plastic cone.

17. The treatment system of claim 12, wherein the dosimeter comprises an independent, secondary real-time dosimeter.

18. The treatment system of claim 12, wherein the dosimeter is deployed as a dose servo mechanism.

19. The treatment system of claim 12, wherein the dosimeter is deployed as a safety interlock to limit a beam current of the linear accelerator to within an acceptable range.

20. The treatment system of claim 12, wherein the dosimeter comprises a toroid.

21. The treatment system of claim 12, wherein the dosimeter comprises a transmission foil.

22. The treatment system of claim 12, wherein the dosimeter comprises a capacitive-coupled detector.

23. The treatment system of claim 12, wherein the electron applicator is configured to provide a 70 cm or less source-to-skin (SSD) FLASH radiotherapy treatment of tumors.

24. A method of treating a tumor, the method comprising:
    generating a high dose radiation;
    collimating the high dose radiation to form a beam of electrons;
    outputting the beam of electrons to an electron applicator;
    measuring, at the electron applicator, a dose of the beam of electrons in real-time;
    collimating, at the electron applicator, the beam of electrons after measuring the dose of the beam of electrons to form a collimated beam of electrons; and shaping, at the electron applicator, the collimated beam of electrons to substantially match a shape of the tumor.

25. The method of treating a tumor of claim 24, wherein the high dose radiation comprises FLASH radiation.

26. The method of treating a tumor of claim 25, wherein the electronic applicator comprises a 70 cm or less source-to-skin distance (SSD).

27. The method of treating a tumor of claim 25, further comprising:
   installing custom cut-outs at a distal end of the electron applicator to shape a radiation field to a treatment area.

28. The method of treating a tumor of claim 24, further comprising:
   installing the electronic applicator for electron FLASH treatments; and
   removing the electronic applicator for conventional mode treatments.

\* \* \* \* \*